US010799631B2

(12) United States Patent
Barmaimon et al.

(10) Patent No.: US 10,799,631 B2
(45) Date of Patent: Oct. 13, 2020

(54) AUTOMATIC INJECTION DEVICE HAVING A MAGNETIC DRIVE SYSTEM

(71) Applicant: FLEXTRONICS AP, LLC, San Jose, CA (US)

(72) Inventors: Eyal Barmaimon, Haifa (IL); Lior Shtram, Tel Aviv (IL); Boaz Kalisch, Haifa (IL); Ronny Bellan, Nazareth (IL); Nadav Cohen, Haifa (IL); Shai Finkman, Haifa (IL); Yuval Harel, Rakefet (IL)

(73) Assignee: FLEXTRONICS AP, LLC, San Jose, CA (US)

( * ) Notice: Subject to any disclaimer, the term of this patent is extended or adjusted under 35 U.S.C. 154(b) by 636 days.

(21) Appl. No.: 15/436,524

(22) Filed: Feb. 17, 2017

(65) Prior Publication Data

US 2017/0239414 A1    Aug. 24, 2017

Related U.S. Application Data

(60) Provisional application No. 62/297,356, filed on Feb. 19, 2016.

(51) Int. Cl.
*A61M 5/145* (2006.01)
*A61M 5/142* (2006.01)
(Continued)

(52) U.S. Cl.
CPC ........ *A61M 5/1456* (2013.01); *A61M 5/1452* (2013.01); *A61M 5/14248* (2013.01);
(Continued)

(58) Field of Classification Search
CPC .. A61M 5/1456; A61M 5/20; A61M 5/31515; A61M 5/31576; A61M 2037/0007; A61M 2205/3317
See application file for complete search history.

(56) References Cited

U.S. PATENT DOCUMENTS 5,482,438 A     1/1996  Anderson et al.
9,364,614 B2 *  6/2016  Nagel ...................... A61M 5/30
(Continued)

FOREIGN PATENT DOCUMENTS

CN      1697666 A    11/2005
CN    104394913 A     3/2015
(Continued)

OTHER PUBLICATIONS

International Search Report and Written Opinion dated Jun. 8, 2017, corresponding application PCT/US2017/018504.
(Continued)

*Primary Examiner* — Kevin C Sirmons
*Assistant Examiner* — Tezita Z Watts
(74) *Attorney, Agent, or Firm* — Volpe and Koenig, P.C.

(57) ABSTRACT

An automatic injection device has an insertion needle configured to be inserted into a patient and a drug container which contains a pharmaceutical product. The drug container includes a plunger. The automatic injection device also has a fluid path which fluidly connects the drug container to the insertion needle. The automatic injection device further has a drive system configured to cause linear movement of the plunger to force the pharmaceutical product into the fluid path. The drive system has a driving element and a movable element. The automatic injection device additionally has electronics configured to provide a signal to the drive system to move the plunger. The movable element has an outer magnet at least partially surrounding the drug container and an inner magnet inside the drug container.

9 Claims, 6 Drawing Sheets

(51) Int. Cl.
*A61M 5/20* (2006.01)
*A61M 5/315* (2006.01)

(52) U.S. Cl.
CPC .......... *A61M 5/20* (2013.01); *A61M 5/31515* (2013.01); *A61M 5/31576* (2013.01); *A61M 2005/14252* (2013.01); *A61M 2005/14573* (2013.01); *A61M 2207/00* (2013.01)

(56) References Cited

U.S. PATENT DOCUMENTS

| | | |
|---|---|---|
| 2003/0055380 A1 | 3/2003 | Flaherty |
| 2006/0030816 A1* | 2/2006 | Zubry .................... A61M 5/24 604/131 |
| 2011/0301566 A1* | 12/2011 | Schaefer .......... A61M 5/14546 604/500 |
| 2013/0274655 A1 | 10/2013 | Jennings et al. |
| 2016/0074587 A1 | 3/2016 | Searle et al. |
| 2016/0367751 A1 | 12/2016 | Bazargan et al. |
| 2017/0239414 A1 | 8/2017 | Barmaimon et al. |
| 2017/0312788 A1* | 11/2017 | Amaravadi ........... E21B 21/065 |

FOREIGN PATENT DOCUMENTS

| | | |
|---|---|---|
| EP | 0110117 A2 | 6/1984 |
| WO | 2011133724 A2 | 10/2011 |
| WO | 2012072555 A1 | 6/2012 |
| WO | 2013026850 A1 | 2/2013 |
| WO | 2015139775 A1 | 9/2015 |
| WO | 2018027937 A1 | 2/2018 |

OTHER PUBLICATIONS

International Search Report and Written Opinion dated Jul. 5, 2019, corresponding application PCT/US2019/027136.
Chinese Office Action dated May 7, 2020 for the Chinese Patent Application No. 201780012114.X.

* cited by examiner

AUTOMATIC INJECTION DEVICE HAVING A MAGNETIC DRIVE SYSTEM

PRIORITY CLAIM

This application claims priority under 35 U.S.C. § 119 to U.S. Provisional Application No. 62/297,356, filed on Feb. 19, 2016 which is expressly incorporated by reference herein in its entirety.

FIELD OF INVENTION

The present disclosure relates to an automatic injection device, and, in particular, to an automatic injection system having a magnetic drive system.

BACKGROUND

Injection devices are used to deliver pharmaceutical products such as biologics and medications to a patient (i.e., a person or animal). A syringe and needle is an example of a widely-used injection device. This basic system typically involves a person manually moving a plunger portion of the syringe to force the pharmaceutical product through the needle and into the patient. Other injection devices have been developed to deliver pharmaceutical products automatically at the touch of a button or the actuation of a switch. These devices are advantageous in that they allow a patient to more easily self-administer the pharmaceutical product. Moreover, some automatic injection devices allow for slow or periodic delivery of the pharmaceutical product as needed, which is typical procedure for patients dependent on insulin injections, for example.

However, there is a need for automatic injection devices to provide injection control in compact device such that the device is easy to handle and discrete for a patient who may wear the device for an extended period of time. Moreover, the elements of the device should be configured for easy replacement of the drug container when the previous container is empty while minimizing the risk of contamination of sterile components.

The present disclosure is direction to an automatic injection device which addresses these needs and the associated problems of the prior art.

SUMMARY

In one aspect, the present disclosure is directed to an automatic injection device. The automatic injection device includes an insertion needle configured to be inserted into a patient and a drug container which contains a pharmaceutical product. The drug container includes a plunger. The automatic injection device also includes a fluid path which fluidly connects the drug container to the insertion needle. The automatic injection device further includes a drive system configured to cause linear movement of the plunger to force the pharmaceutical product into the fluid path. The drive system includes a driving element and a movable element. The automatic injection device additionally includes electronics configured to provide a signal to the drive system to move the plunger. The movable element includes an outer magnet at least partially surrounding the drug container and an inner magnet inside the drug container In another aspect, the present disclosure is directed to a cartridge for an automatic injection device. The cartridge includes a space for receiving a drug container which contains a pharmaceutical product. The cartridge also includes a drive system comprising a driving element and a movable element, the movable element including an outer magnet which is configured to be moved linearly in the space for receiving a drug container by the driving element.

In yet another aspect, the present disclosure is directed to a method of assembling an automatic injection device. The method includes positioning a diametrically magnetized inner magnet in a drug container which contains a pharmaceutical product and inserting the drug container in a through-hole of a diametrically magnetized outer magnet such that the inner magnet is aligned with the through-hole. The outer magnet is linearly movable on an outside of the drug container by a driving element of the automatic injection device in order to move the inner magnet inside the drug container.

DETAILED DESCRIPTION OF THE PREFERRED EMBODIMENT(S)

Disclosed embodiments pertain to a drive system for an automatic injection device. The drive system provides an input force to move an element of the automatic injection device to control delivery of a pharmaceutical product to a patient. For example, the drive system may be configured to control movement of a plunger placed in a drug container. Further movement of the plunger inside the drug container pushes the pharmaceutical product through a fluid path and to a insertion needle which connects to the patient. This controlled movement of the plunger allows for metered delivery of the pharmaceutical product according to desired parameters.

The disclosed drive system includes features which allow for precise control over plunger movement while providing a small form factor which allows the automatic injection device to be compact. The disclosed drive system utilizes magnetic elements which harness a magnetic force to create a connection between an element outside of the drug container and an element inside the drug container. This configuration can be provided in a small space and also does not require the drive element to physically enter the drug container to push the plunger.

Figure 1:
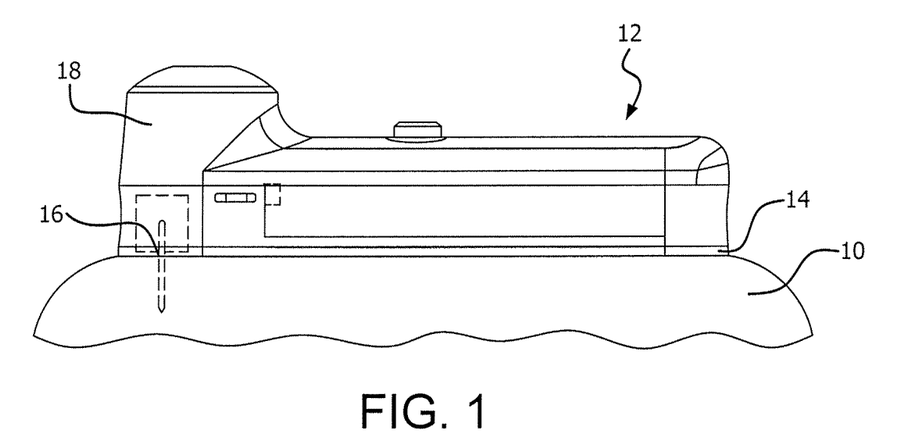
FIG. 1 is a side view illustration of an exemplary automatic injection device positioned on a patient.

FIG. 1 is a depiction of an exemplary embodiment of an automatic injection device 12 on a patient 10. The patient 10 is not limited and can be any organism which may receive an injection. The device 12 is configured to deliver a pharmaceutical product to the patient 10 automatically. This means that the device 12 is controlling the injection in some way such that the system differs from other injection systems where manual input alone causes the injection (i.e., a conventional syringe and needle system or other available systems). The automatic aspect of the device 12 may additionally or alternatively relate to the duration of the injection, controlled injection intervals, a delay between input and injection, etc.

The device 12 includes a base 14 that contacts the patient's skin. The device 12 includes a insertion needle 16 which enters the patient 12 to deliver a pharmaceutical product, such as insulin, to the patient. An example of an automatic injection device which includes many of the features that may be incorporated into the device 12 is described in WO 2017/007952, which is herein incorporated by reference. However, it should be understood that the device 12 is not limited to the automatic injection device described therein or the exemplary embodiments described below. An automatic injection device consistent with this disclosure may include some of the features described herein but is not limited thereto. For example, a disclosed automatic injection device may resemble a syringe and needle system or other injection system which is adapted for automatic injections via the features described herein.

Figure 2:
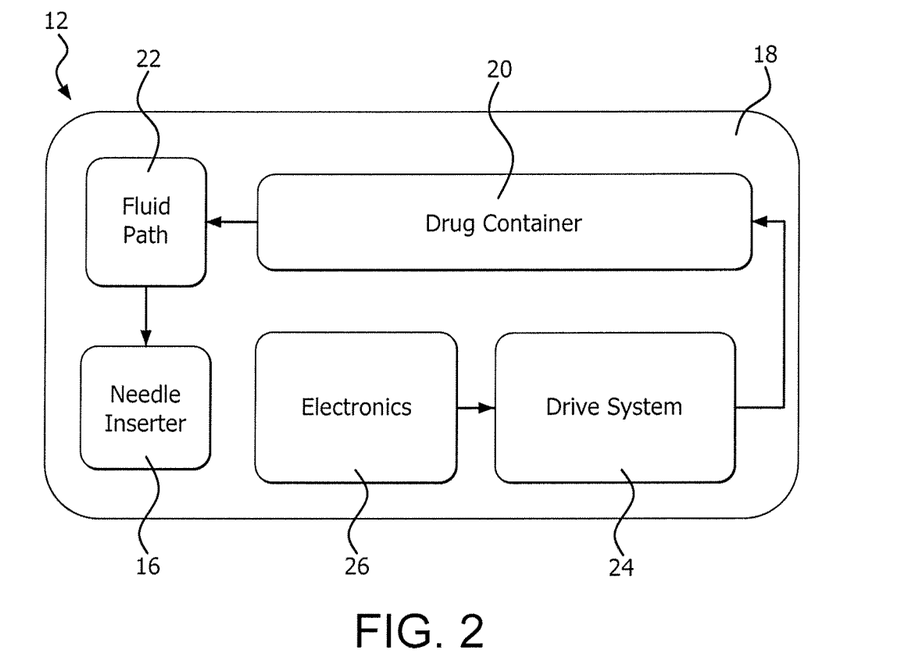
FIG. 2 is a schematic illustration of the components of an automatic injection device consistent with disclosed embodiments.

FIG. 2 is a schematic illustration of the automatic injection device 12 and the basic features of the device 12 which facilitate automatic injections of a pharmaceutical product into the patient 10. The device 12 preferably includes a housing 18 which holds at least some of the features of the device 12. In addition to the insertion needle 16, these features preferably include a drug container 20, a fluid path 22, a drive system 24, and electronics 26. These features work in conjunction with each other to automatically deliver a pharmaceutical product to the patient 10 according to desired parameters.

The drug container 20 is a containing element which supplies the pharmaceutical product. The drug container 20 may be a vial, syringe, or the like and includes a space for containing the pharmaceutical product, which is not limited to a particular substance. The pharmaceutical product may be any substance which is considered one or more of a drug, biologic, medication, or placebo, for example. The drug container 20 is preferably a hollow cylindrical tube which receives the pharmaceutical product. However, it should be understood that other configurations are possible.

In the device 12, the drug container 20 is fluidly connected to the insertion needle 16 by the fluid path 22. The fluid path 22 may be a physical connecting channel which serves as a conduit for delivering the pharmaceutical product from the drug container 20 to the insertion needle 16 and ultimately into the patient 10. The fluid path 22 may include additional structure, including actuating mechanisms which initiate delivery of the pharmaceutical product and/or control mechanisms which meter an amount of product which is delivered to the patient 10 at any particular time. The fluid path 22 may include an element or mechanism which is configured to establish the connecting channel, such as a puncturing needle or the like. The fluid path 22 may be associated with a start button or control switch or even the electronics 26 which control an element of the fluid path 22 (e.g., a valve) in order to start or stop the delivery of the pharmaceutical product. It should be understood, however, that the fluid path 22 may be a passive system component in at least some embodiments.

The drive system 24 and electronics 26 provide the automatic aspect of the injections via device 12. For example, the drive system 24 is a mechanical system which physically moves an element of the device 12 to move the pharmaceutical product from the drug container 20 to into the fluid path 22 and ultimately into the patient 10. For example, the drive system 24 may be configured to move a plunger positioned inside the drug container 20 to force the pharmaceutical product out of the drug container 20. The drive system 24 includes magnetic elements, as will be described in more detail herein. The electronics 26 include features such as control circuitry, processing devices, memory, I/O devices, etc. and are configured to control the drive system 24 such that the pharmaceutical product is delivered according to desired parameters. For example, the electronics may translate an input signal and provide a signal to the drive system 24 to move a plunger inside the drug container 20 by a selected amount.

Figure 3:
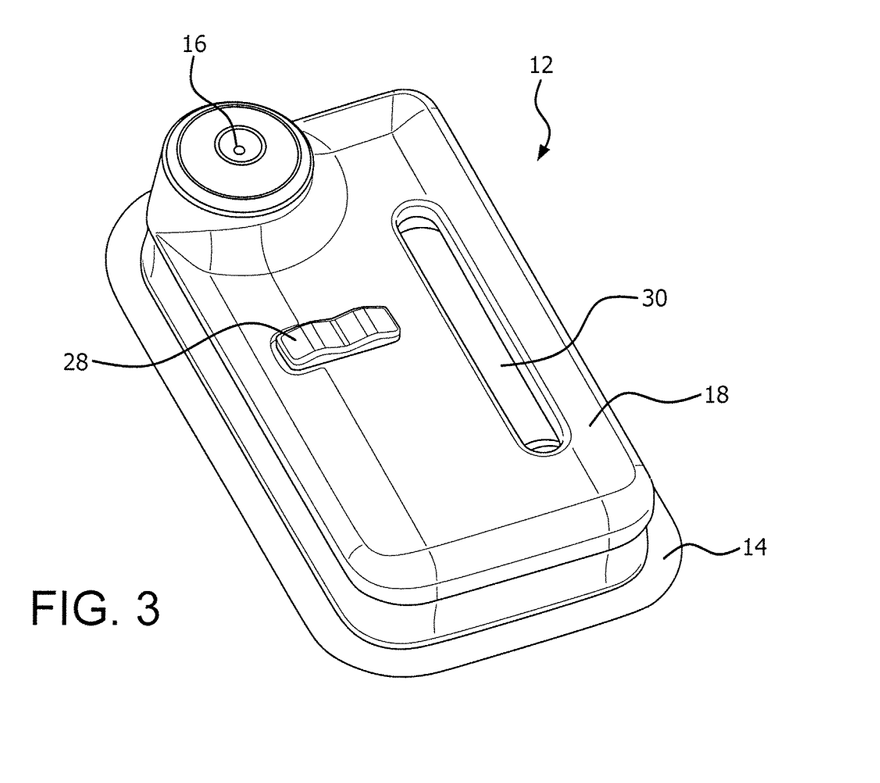
FIG. 3 is a perspective view of a top side of the automatic injection device.
Figure 4:
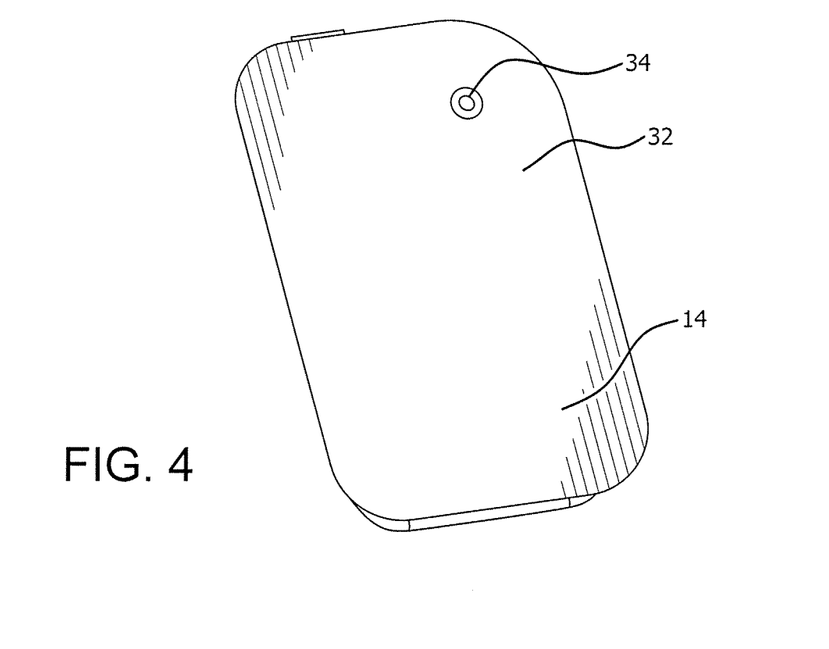
FIG. 4 is a perspective view of a bottom side of the automatic injection device.

FIGS. 3 and 4 further illustrate an exemplary embodiment of the automatic injection system 12. FIG. 3 illustrates a first side of the device 12, including the housing 18 which rests on top of the base 14. The housing 18 is illustrated as being rectangular, but can include any shape. The housing 18 may include optional features such as at least one control switch 28 which provides an input signal to the electronics 26 and/or a window 30 which provides a view of the drug container 20 and thus the current fluid level.

FIG. 4 illustrates a second side of the device 12 including a bottom surface of the base 14. The bottom surface 32 includes an opening 34 for receiving the insertion needle 16 therethrough. In use, the device 12 is placed against the patient 10 with the bottom surface 32 of the base 14 against the skin. An injection needle extends through the opening 34 and into the patient 10 to deliver the pharmaceutical product. The bottom surface 32 may include an adhesive material thereon to adhere the device 12 to the patient 10 for either a short or long period of time, depending on the particular use of the device 12.

Figure 5:
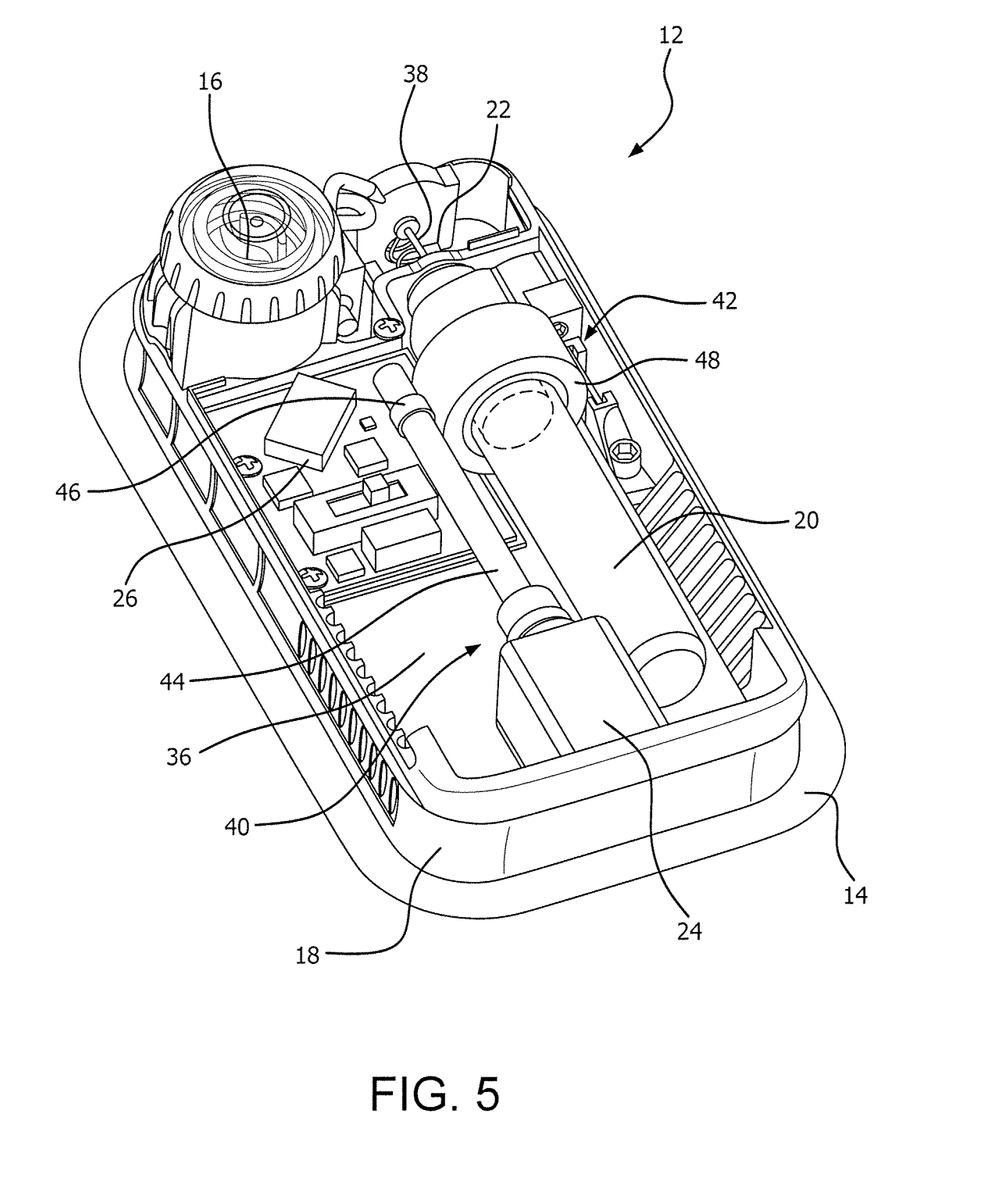
FIG. 5 is a perspective view of the internal components according to an embodiment of the automatic injection device.

FIG. 5 illustrates the device 12 with the top portion of the housing 18 removed such that the internal features are shown in an enclosed space 36 formed by a lower portion of the housing 18 and the base 14. The device 12 includes exemplary embodiments of the insertion needle 16, the drug container 20, the fluid path 22, the drive system 24, and the electronics 26. The enclosed space 36 houses at least the drug container 20, drive system 24, and electronics 26 such that the elements are positioned inside of the housing 18.

The fluid path 22 in this embodiment includes a connector 38 which physically connects to the drug container 20 to establish a connection channel between the interior of the drug container 20 and the insertion needle 16. In the illustrated embodiment, the insertion needle 16 is positioned perpendicular to the drug container 20 such that the path of the pharmaceutical product is to travel out of the drug container 20 and laterally into the area of the insertion needle 16 via the fluid path 22. The pharmaceutical product subsequently travels vertically downward through the insertion needle 16 and into the patient 10. This configuration is exemplary, however, and disclosed embodiments are not limited thereto. In other embodiments, the insertion needle 16 may be aligned in the same direction as the drug container 20 and/or the fluid path 22.

The drive system 24 includes a driving element 40 and a movable element 42. The driving element 40 is positioned in the space 36 and is electronically connected to the electronics 26. The driving element 40 is a device which produces mechanical motion, such as a motor or the like. The movable element 42 is operably connected to the driving element 40 such that the driving element 40 controls the motion of the movable element 42. In an exemplary embodiment, the driving element 40 includes a shaft 44 and a connector 46 which is movable on the shaft 44 by the driving element 40. The movable element 42 includes an outer collar 48 which surrounds the drug container 20 and which movement thereof is configured to cause the pharmaceutical product to exit the drug container 20 and enter the fluid path 22.

Figure 6:
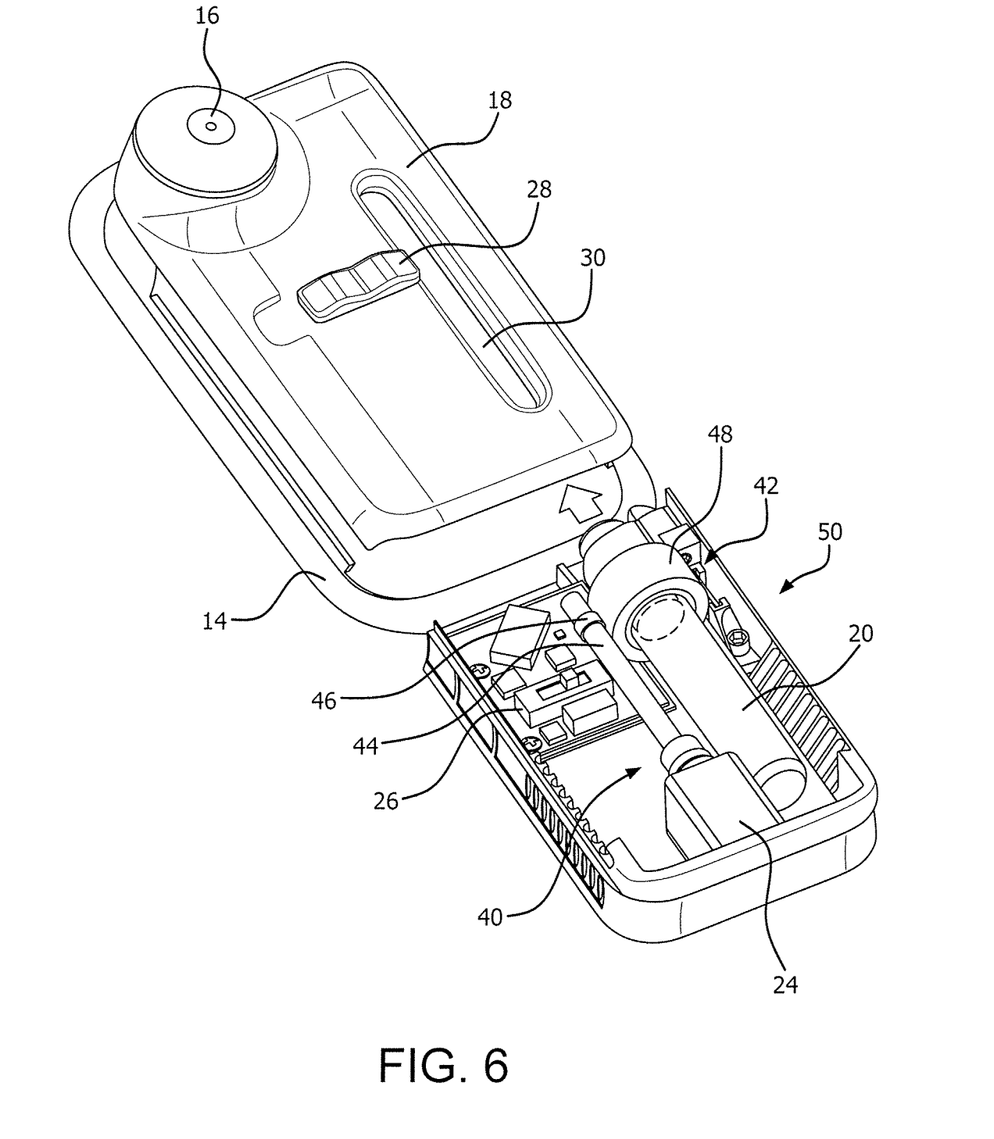
FIG. 6 is a perspective view of a separated housing and cartridge according to an embodiment of the automatic injection device.

FIG. 6 illustrates an embodiment of the device 12 which includes drug container 20, drive system 24, and electronics 26 as a removable cartridge 50 relative to the housing 18, the fluid path 22, and the insertion needle 16. The drug container 20 is removable from the cartridge 50 for replacement after use. This configuration allows for insertion and replacement of the drug container 20 and helps with separating sterile components (e.g., the housing 18 and the drug container 20) from non-sterile components (e.g., the cartridge 50). The drug container 20 is insertable into the outer collar 48 of the drive system 24 in order to operably connect the movable element 42 to the drug container 20.

Figure 7:
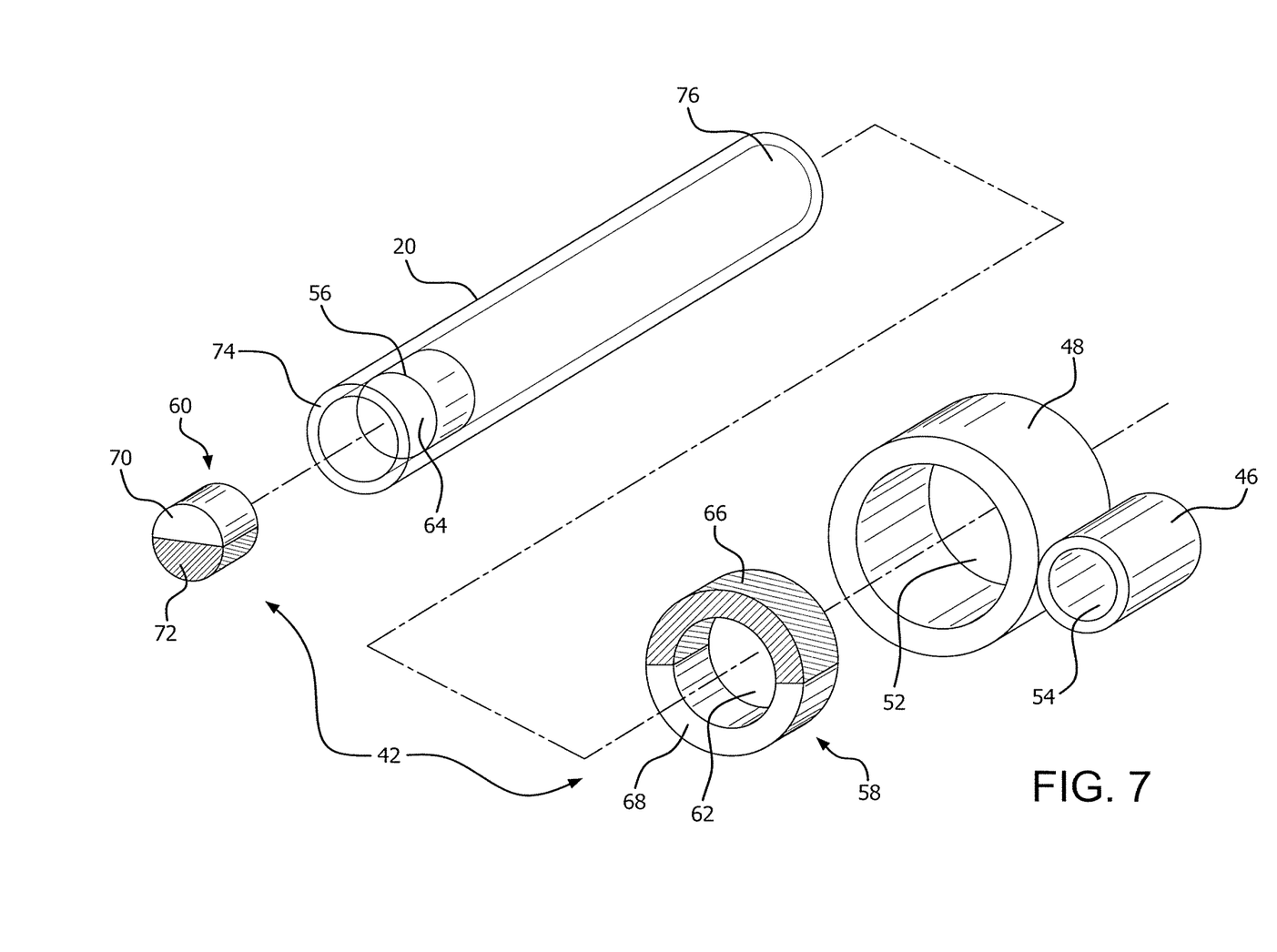
FIG. 7 is an exploded view of a movable member of a drive system of the automatic injection device.

FIG. 7 illustrates an exploded view of the movable element 42 in relation to the drug container 20. As shown, the movable element 42 includes the outer collar 48 and the attached connector 46. The outer collar 48 is a generally cylindrical ring which includes a through-hole 52. The outer collar 48 may be generally formed of a soft magnetic alloy. The connector 46 is also a generally cylindrical ring which includes a through-hole 54 for receiving the shaft 44, although other configurations are possible. The connector 46 is smaller than the outer collar 48 and attached to an outer wall of the outer collar 48 such that an axis of the through-hole 52 is parallel to an axis of the through-hole 54.

In an exemplary embodiment, the drug container 20 further includes a plunger 56 which is positioned inside of the drug container 20 and is configured to move the pharmaceutical product out of the drug container 20 via movement thereof. The plunger 56 is preferably sized to create a sealed arrangement inside of the drug container 20, much like a typical syringe plunger. The plunger 56 is disc-shaped or otherwise shaped to match the drug container 20.

The movable element 42 further includes a magnetic arrangement which translates movement of the outer collar 48 into movement of the plunger 56. The movable element 42 preferably includes an outer magnet 58 and an inner magnet 60. The outer magnet 58 is a generally cylindrical ring including a through-hole 62. The outer magnet 58 is positioned in the through-hole 52 of the outer collar 48 and surrounds the exterior of the drug container 20. The outer collar 48 and outer magnet 58 may be attached to each other, such as through magnetic attraction, friction fit, adhesive, fasteners, etc. In an alternative embodiment, the outer collar 48 and the outer magnet 58 may be the same component (e.g., the outer collar 48 is diametrically magnetized or includes a magnetized portion).

The inner magnet 60 is generally cylindrical and may be solid or in the form of a ring. Other shapes of the inner magnet 60 are also possible (e.g., U-shaped, spherical, square, etc.) The inner magnet 60 is sized to fit within the drug container 20 and abuts a first side 64 of the plunger 56. In an alternative embodiment, the inner magnet 60 and the plunger 58 are the same component (e.g., the plunger 58 is diametrically magnetized or includes a magnetized portion). In this alternative embodiment, the plunger 58 and inner magnet 60 are an integral component which may include an acceptable material (e.g., a sterilized plastic) on a side which faces and contacts the pharmaceutical product.

The outer magnet 58 and inner magnet 60 are configured to create a magnetic field which maintains a relative position between the two. For example, the outer magnet 58 may be diametrically magnetized with a first radial side 66 of the outer magnet 58 being a first pole and a second radial side 68 of the outer magnet being a second pole. The inner magnet 60 may be diametrically magnetized in a direction opposite from the outer magnet 58. For example, the inner magnet 60 may include a first radial side 70 which is aligned with the first radial side 66 of the outer magnet 58 and which is an opposite pole of the first radial side 66 of the outer magnet 58. Similarly, the inner magnet 60 may include a second radial side 72 which is aligned with the second radial side 68 of the outer magnet 58 and which is an opposite pole of the second radial side 68 of the outer magnet 58. In this way, the first side 66 of the outer magnet 58 is attracted to the first side 70 of the inner magnet 60 and the second side 68 of the outer magnet 58 is attracted to the second side 72 of the inner magnet 60. With this configuration, the inner magnet 60 can be positioned in the through-hole 62 of the outer magnet 58 in equilibrium such that inner magnet 60 will follow movement of the outer magnet 58.

The outer magnet 58 and inner magnet 60 may be formed from any of a variety of magnetic materials (e.g., magnetized metallic materials, rare earth magnets, etc.). In some embodiments, one or more of the outer magnet 58 and/or the inner magnet 60 may be an electromagnet. For example, the outer magnet 58 may be an electromagnet which can be switched on and off (and/or reverse polarization) to control the magnetic field in and around the movable element 42. In one embodiment, the outer magnet 58 may be controllable (e.g., as an electromagnet) to selectively repel and/or attract the inner magnet 60 to cause the inner magnet 60 to move within the drug container 20.

Figure 8:
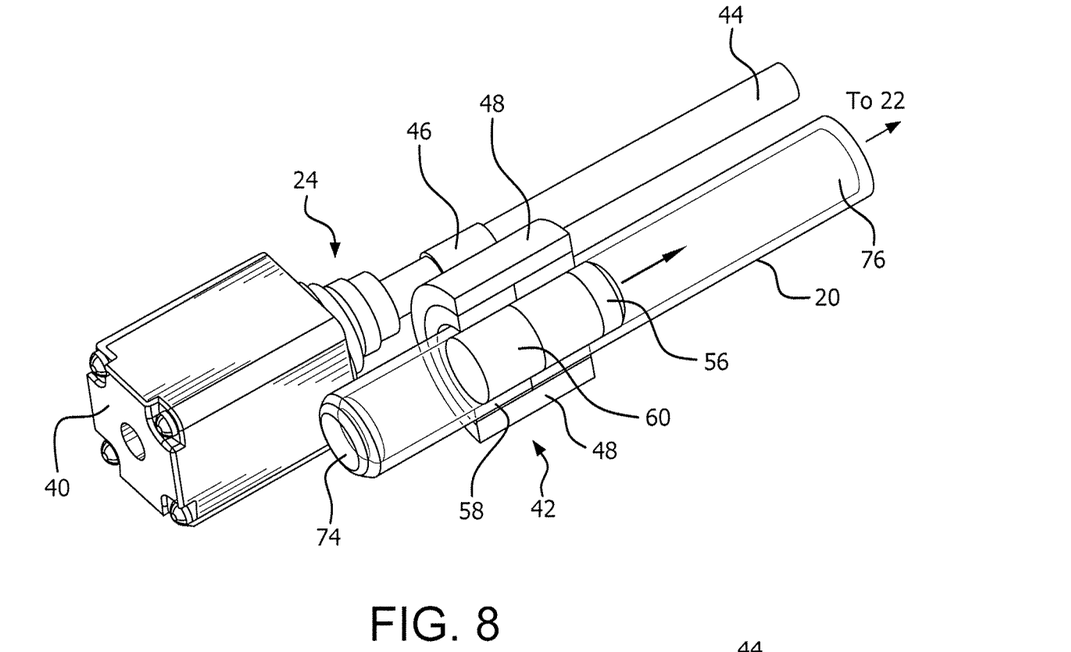
FIG. 8 is a perspective view of the drive system including the movable member in a first position.
Figure 9:
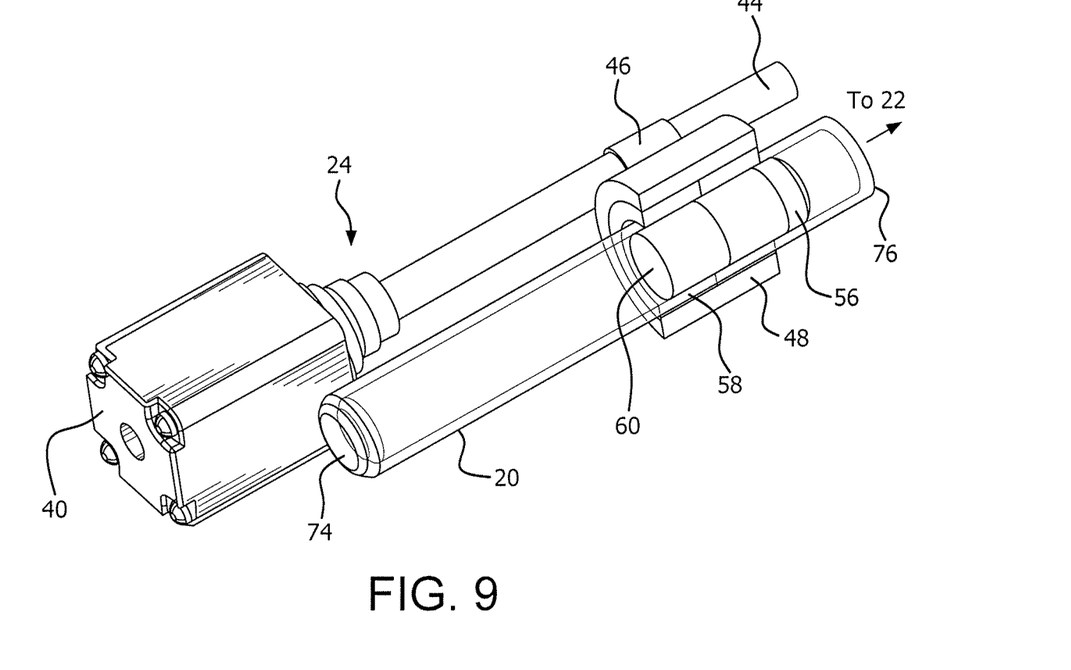
FIG. 9 is a perspective view of the drive system including the movable member in a second position.

FIGS. 8 and 9 further illustrate the functioning of the drive system 24 in relation to the drug container 20. As shown, the inner magnet 60 is positioned in the drug container 20 and abuts the plunger 56 (or acts as the plunger is alternative embodiments). The outer magnet 58 is positioned around the exterior of the drug container 20, in alignment with the inner magnet 60. In some embodiments, two outer magnet 58 and two inner magnets 60 may be stacked in a longitudinal direction to establish a sufficient magnetic force between the two. The outer collar 48 surrounds the outer magnet 58 (or is the outer magnet 58 in alternative embodiments). The connector 46 is positioned on the shaft 44 which is attached to the driving element 40.

In use, the driving element 40 is configured to linearly move the connector 46 along the shaft 44. This may be accomplished through a threaded shaft and connector where the driving element 40 rotates the threaded shaft 44 to move the connector 46. Other configurations which cause linear movement of the connector 46 (such as through the use of gears, pulleys, etc.) are also possible. Movement of the connector 46 causes corresponding linear movement of the outer collar 48 and outer magnet 58. In this way, the driving element 40 is configured to cause linear movement of the outer magnet 58 along an outside of the drug container 20, in a longitudinal direction of the drug container 20 (i.e., along a longitudinal axis of the drug container 20.

The movement of the outer magnet 58 in this way along the outside of the drug container 20 causes corresponding movement of the inner magnet 60 inside of the drug container 20. The corresponding movement of the inner magnet 60 is linear movement along the longitudinal axis of the drug container 20. The corresponding movement is enabled by the magnetic attraction between the inner magnet 60 and the outer magnet 58, which penetrates through the surface of the drug container 20.

FIG. 8 illustrates the movable element 42 of the drive system 24 in a first position, with the plunger 56 near a first longitudinal end 74 of the drug container 20. The drive element 40 is configured to move the inner magnet 60 (via the outer magnet 58, outer collar 48, connector 46, and shaft 44) to force the plunger 56 toward a second longitudinal end 76 of the drug container 20.

FIG. 9 illustrates the movable element 42 of the drive system 24 in a second position, with the plunger 56 near the second longitudinal end 76 of the drug container 20. This movement of the plunger 56 forces the pharmaceutical product in the drug container out of an opening near the second longitudinal end 76 and into the fluid path 22 of the device 12. The pharmaceutical product subsequently flows through the flow path 22 and into the patient 10 through the insertion needle 16.

The electronics 26 are configured to calibrate movement of the shaft 44, connector 46, and/or outer collar 48 such that precise control over movement of the plunger 50 is possible. In this way, the driving element 40 controls (via control signals from the electronics 26) an amount, timing, and speed of an automatic injection of a pharmaceutical product from the drug container 20 into the patient 10.

Consistent with disclosed embodiments, the driving element 40 causes linear movement of the outer magnet 58 which causes linear movement of the inner magnet 60. The illustrated embodiments further include the shaft 44, connector 46, outer collar 48, and plunger 56 as additional components which may be included in the operative configuration. However, some or all of these components may be omitted and/or substituted by similar components. For example, the driving element 40 may directly move the outer magnet 58, which moves the plunger 56 via the inner magnet 60. In some embodiments, the inner magnet 60 is configured as the plunger 56 such that movement of the inner magnet 60 directly forces the pharmaceutical product out of the drug container 20.

Moreover, it should be understood that the relative orientation of the disclosed components may be varied. In the illustrated embodiment, the driving element 40 "pushes" the pharmaceutical product out of the second longitudinal end 76 of the drug container 20. In other embodiments, the first longitudinal end 74 of the drug container 20 may be connected to the fluid path 22 and the plunger 56 and pharmaceutical product arranged on an opposite side of the inner magnet 60 such that driving element 40 "pulls" the plunger 56 to force the pharmaceutical product out of the drug container 20.

The drug container 20 may be a single-use component which is replaced after use. For example, an empty drug container 20 may be removed from the cartridge 50 (FIG. 6) and replaced with a full drug container 20. Each drug container 20 may be manufactured with an inner magnet 60 already in place (either in addition to the plunger 56 or to act as the plunger 56). In other embodiments, the inner magnet 60 may be added to the drug container 20 before it is loaded into the cartridge 50. In an assembly process, the drug container 20 may be slid into the outer collar 48/outer magnet 58 elements in the cartridge 50 and then the cartridge 50 inserted into the housing 18 of the device 12. It should be understood, however, that this is an exemplary configuration and that other embodiments are possible. For example, the housing 18 may be a single unit which includes an opening for receiving the drug container 20.

The disclosed features are applicable to any injection device in order to cause movement of a plunger without physically entering the drug container. The magnetic arrangement allows movement of a component outside of the drug container (e.g., the outer magnet) to cause corresponding movement of a component inside the drug container (e.g., the inner magnet) without physically breaking a barrier into the drug container. This configuration is especially applicable to an automatic injection device where a driving element is present. The magnetic arrangement allows the driving element to move the plunger in a small form factor which enables a compact device.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. An automatic injection device, comprising:
   an insertion needle configured to be inserted into a patient;
   a drug container which contains a pharmaceutical product, the drug container including a plunger;
   a fluid path which fluidly connects the drug container to the insertion needle;
   a drive system configured to cause linear movement of the plunger to force the pharmaceutical product into the fluid path, the drive system comprising a driving element and a movable element, the drive system disposed within a cartridge, and wherein the cartridge is configured to be inserted into a housing of the automatic injection device; and
   electronics configured to provide a signal to the drive system to move the plunger,
   wherein the movable element includes an outer magnet at least partially surrounding the drug container, an inner magnet inside the drug container, and an outer collar including a through-hole which receives the outer magnet,
   the outer magnet is ring-shaped and includes a through-hole which receives the drug container,
   the inner magnet is disc-shaped and is aligned with the through-hole of the outer magnet, and
   the outer magnet is diametrically magnetized in a first direction and the inner magnet is diametrically magnetized in an opposite second direction such that the inner magnet follows linear movement of the outer magnet.

2. The automatic injection device of claim 1, wherein the driving element includes a shaft and a connector, and the outer magnet is configured to be moved linearly along the outside of the drug container by movement of the connector along the shaft.

3. The automatic injection device of claim 2, wherein the outer collar is connected to the shaft of the driving element by the connector.

4. The automatic injection device of claim 3, wherein the connector includes a through-hole which includes an axis which is parallel to an axis of the through-hole of the outer collar.

5. The automatic injection device of claim 1, wherein the driving element is a motor.

6. The automatic injection device of claim 1, wherein the inner magnet abuts a side of the plunger and exerts a force on the plunger to move the plunger longitudinally inside the drug container.

7. The automatic injection device of claim 1, wherein the plunger and the inner magnet are integral.

8. The automatic injection device of claim 1, wherein the housing
   which defines a space which receives the drug container, the drive system, and the further comprising
   a base which is configured to contact the patient.

9. The automatic injection device of claim 1, wherein the outer magnet is an electromagnet which is controllable by the driving element.

* * * * *